United States Patent
Herskovic

(12) 
(10) Patent No.: US 10,967,198 B2
(45) Date of Patent: Apr. 6, 2021

(54) BRACHYTHERAPY STENT CONFIGURATIONS

(71) Applicant: Arnold Herskovic, Chicago, IL (US)

(72) Inventor: Arnold Herskovic, Chicago, IL (US)

( * ) Notice: Subject to any disclaimer, the term of this patent is extended or adjusted under 35 U.S.C. 154(b) by 0 days.

(21) Appl. No.: 16/425,497

(22) Filed: May 29, 2019

(65) Prior Publication Data

US 2020/0376293 A1  Dec. 3, 2020

(51) Int. Cl.
| | |
|---|---|
| *A61N 5/10* | (2006.01) |
| *A61L 31/02* | (2006.01) |
| *A61L 31/04* | (2006.01) |
| *A61L 31/18* | (2006.01) |
| *A61L 31/12* | (2006.01) |

(52) U.S. Cl.
CPC .......... *A61N 5/1002* (2013.01); *A61L 31/022* (2013.01); *A61L 31/04* (2013.01); *A61L 31/12* (2013.01); *A61L 31/18* (2013.01); *A61N 5/1007* (2013.01); *A61L 2400/16* (2013.01); *A61N 2005/1021* (2013.01); *A61N 2005/1025* (2013.01)

(58) Field of Classification Search
CPC .............. A61N 2005/1094; A61N 5/00; A61N 5/1002; A61N 5/1007
See application file for complete search history.

(56) References Cited

U.S. PATENT DOCUMENTS

| | | | |
|---|---|---|---|
| 4,819,618 A | 4/1989 | Liprie | |
| 5,575,749 A | 11/1996 | Liprie | |
| 5,713,828 A | 2/1998 | Coniglione | |
| 6,053,858 A * | 4/2000 | Bueche | ............... A61N 5/1002 |
| | | | 600/3 |
| 6,442,822 B1 | 9/2002 | Liprie | |
| 6,506,145 B1 | 1/2003 | Bradshaw | |
| 2002/0055667 A1* | 5/2002 | Mavity | ................ A61N 5/1027 |
| | | | 600/3 |
| 2003/0088146 A1* | 5/2003 | Slater | ................... A61N 5/1027 |
| | | | 600/8 |

OTHER PUBLICATIONS

Isoray, Products: See how Cesium-131 by Isoray is being used, accessed from https:isoray.com/clinicians/products/ on Apr. 12, 2019.

* cited by examiner

*Primary Examiner* — Christine H Matthews
(74) *Attorney, Agent, or Firm* — Cherskov Flaynik & Gurda, LLC

(57) ABSTRACT

The invention describes method for delivering and positioning radio-isotopes. The method uses encapsulating free flowing medicament into a vehicle and positioning the vehicle into the body. Also provided is a system for delivering and positioning radio-isotopes into the body, the system comprising fluid radio-isotope encapsulated in a material.

11 Claims, 5 Drawing Sheets

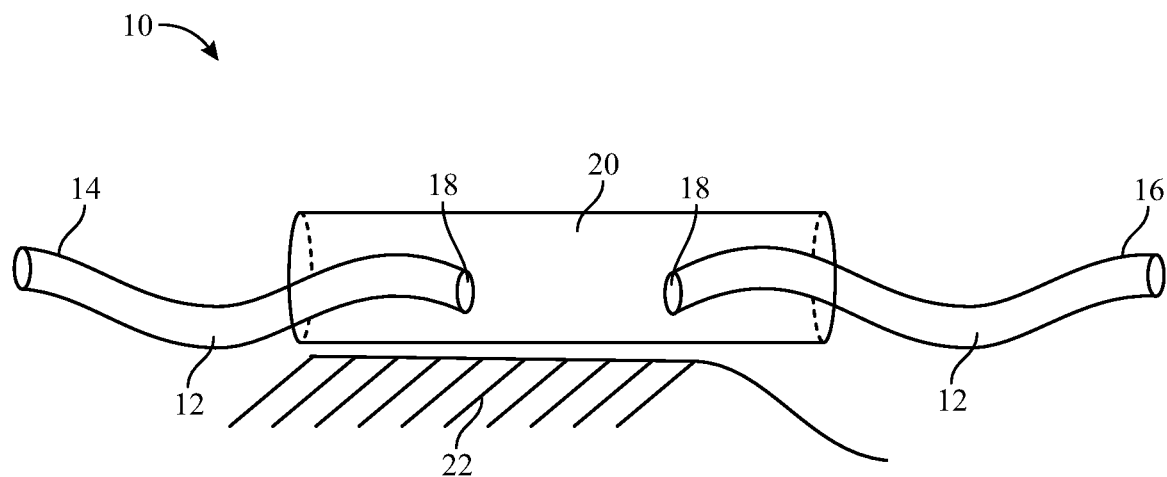
FIG. 1A
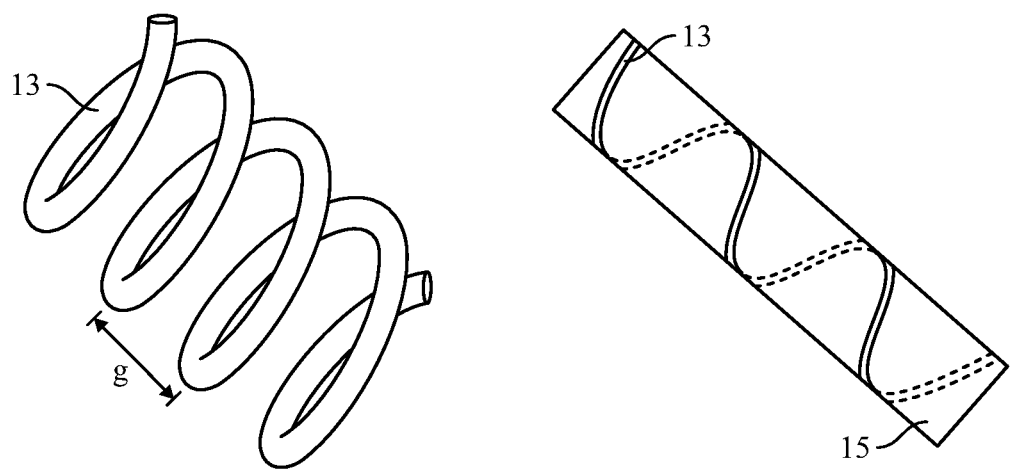
FIG. 1B
FIG. 1C

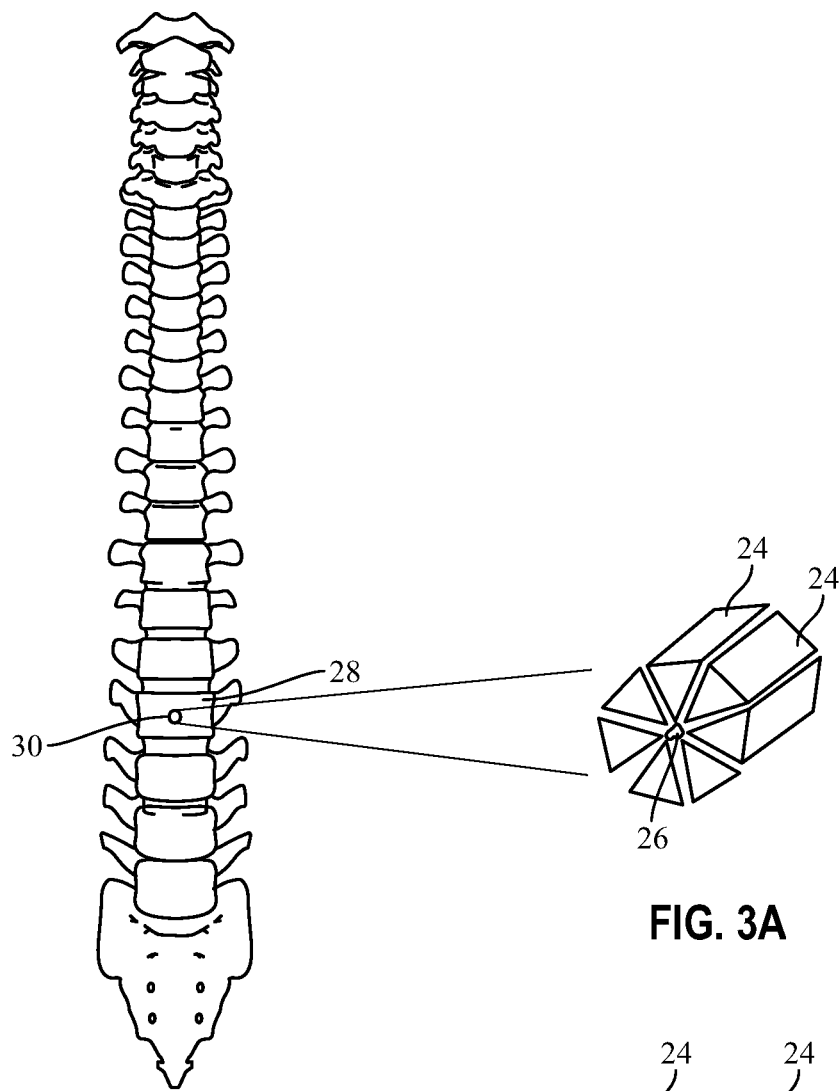
FIG. 2
FIG. 3A
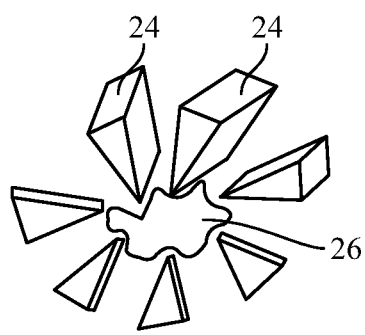
FIG. 3B

BRACHYTHERAPY STENT CONFIGURATIONS

BACKGROUND OF THE INVENTION

1. Field of the Invention

This invention relates to a system and method for delivering medicament, and more specifically this invention relates to radioisotope vehicles and methods for configuring vehicles to optimize in vivo treatment.

2. Background of the Invention

There are a variety of ways to access and treat tissues in vivo. Often, one or a plurality of apertures near the treatment sight are made to allow access of surgical instruments, sutures, cauterizers, and the like. Cannulas, associated trocars, wire guides, catheters are all vehicles to access the deep tissue treatment sites for the eventual surgical or brachytherapy follow up.

The smaller the intervention physically, the more adaptable to multiple situations. Attempts have been made to miniaturize instruments, stents, etc., to access narrow passageways (called lumens) such as ducts, arteries and veins, and generally hard to reach structures.

Brachytherapy usually involves the positioning of radioactive materials (packaged into discrete individual seeds) at tumor or vascular locations so as to eradicate or shrink the tumors or positively affect revascularization. Commercially available seeds generally have a central core of liquid or powder enclosed in a titanium shell or other rigid material to filter out undesirable radiations. They are then batched by activity.

Sometimes these tumor locations are accessed surgically near the surface (or exposed sites). Other times a large bore injection needle is required to position the radio isotopes into hard to reach areas such as hollowed out vertebrae, the esophagus, small diameter ducts and other situations where direct surgical access is unavailable without causing collateral damage from either external beam radiation or surgical intervention. For example, needles are often relied upon to access the interiors of vertebra for kyphoplasty treatment. Typical needles used for such injections are about 14 gauge diameters. This is because needle bore sizes having an inner diameter of approximately 1.6 mm) are required inasmuch as the smallest radio-isotope seeds have a cross sectional diameter of about 0.8 mm.

State of the art brachytherapy stents and devices are only slightly smaller, with the limiting factor being the size of the radioisotope seeds utilized for treatment. That the seeds have to be a certain size to provide an effective therapeutic dose combined with the fact that seeds are typically not manufactured smaller than 0.8 mm in diameter means that brachytherapy vehicles are too bulky to access small diameter lumens.

Brachytherapy, particularly with very low energy sources has the advantage of minimizing collateral radiation but is very sensitive to optimal seed placement. Either too high a dose or too low may have unfortunate outcomes. Higher doses (e.g. delivered to the tissues adjacent to the sources) have been necessary to deliver a cancerocidal dose to the tumor but this may lead to hemorrhage ulceration fistulization, etc.

Strategies useful to decrease this gradient include the following:
increasing the number of radioactive seeds;
filtration of the radiation emanating from the closest sources;
padding (i.e., increases the distance between radiation sources and sensitive tissues);
increasing the radioactive source energy but while also minimizing exposure of healthy tissues; and
increasing the distance between radiation sources and sensitive tissues.

Additionally, radiation oncologists are most comfortable if an homogenous radiation dose distribution is achieved.

A need exists in the art for a system and method for treating deep seated neoplasms. The system and method should be capable of delivering medicaments through small pores. Also, the system and method could incorporate shielding to prevent in situ over exposure of tissue to radiation.

SUMMARY OF INVENTION

An object of the invention is to provide a system and method for conducting brachytherapy that overcomes many of the drawbacks of the prior art.

Another object of the invention is to provide a system and method for positioning medicament in deep seated tissue sites. A feature of the invention is utilization of fluid-phase medicament encapsulated in reversibly deformable material. An advantage of the invention is that the size, such as the cross diameter, of the deformable vehicle could be minimized. Another advantage is that the vehicle replaces the shielding inherent in solid radioactive seeds.

Still another object of the invention is to provide a system and method for enabling in vivo positioning of radioisotopes in brachytherapy. A feature of the invention is encapsulating free flowing liquid-phase radioisotopes within a solid phase vehicle having semi-radio-opaque characteristics. An advantage of the invention is that the vehicle may be reversibly inserted into heretofore inaccessible tissue sites, such as very narrow ducts, collapsed vertebrae, cavities, surgical sites, and other lumens. Another advantage is that liquid isotopes makes smaller preloaded catheter ribbons, rectangles, triangles, semicircular, and other shaped delivery vehicles feasible.

Briefly, the invention provides a method for delivering and positioning radio-isotopes into the body, the method comprising encapsulating free flowing radio-isotope into a vehicle; and positioning the vehicle into the body.

Also provided is a system for delivering and positioning radio-isotopes into the body, the system comprising fluid radio-isotope encapsulated in a material.

BRIEF DESCRIPTION OF DRAWINGS

The invention together with the above and other objects and advantages will be best understood from the following detailed description of the preferred embodiment of the invention shown in the accompanying drawings, wherein:

FIG. 1A is a schematic elevational view of a brachytherapy stent/sleeve stent configuration, in accordance with features of the present invention;

FIG. 1B is a schematic prospective view of a spiral vehicle, in accordance with features of the present invention;

FIG. 1C is a schematic depiction of an orthopedic medicament delivery device, in accordance with features of the present invention;

FIG. 2 is an elevational view of a vertebral column with an access aperture;

FIG. 3A is perspective view of a plurality of concentrically arranged undeployed brachytherapy vehicles prior to insertion into a vertebral column, in accordance with features of the present invention;

FIG. 3B is a perspective view of deployed brachytherapy vehicles, in accordance with features of the present invention;

DETAILED DESCRIPTION OF THE INVENTION

Figure 4A:
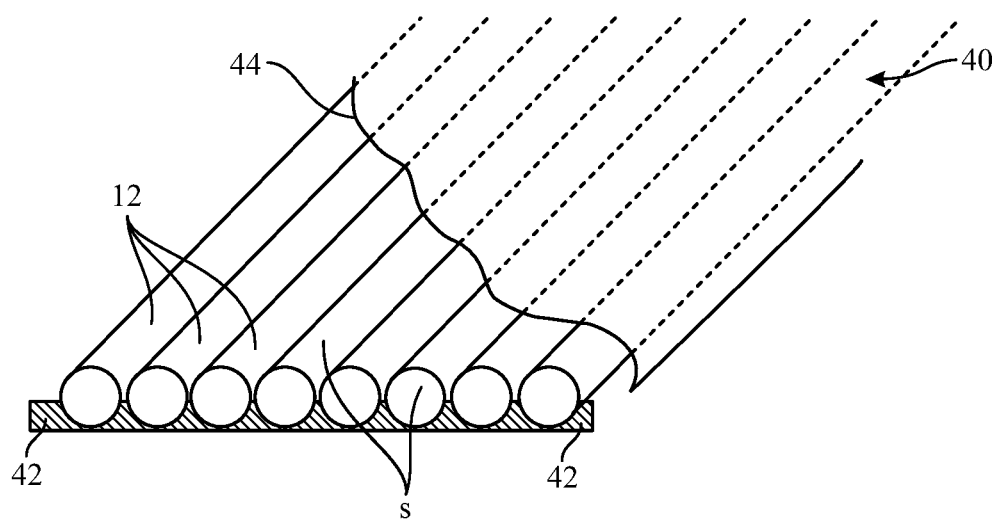
FIG. 4A is a perspective view of an array of brachytherapy vehicles in parallel relation to each other, in accordance with features of the present invention.

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a method and system for inserting and repositioning medicaments in hard to reach spaces within the body. A salient feature of the invention is that the medicaments are fluidized. This allows for replacement of solid phase seeds which leads to miniaturization and manipulation of the physical vehicles containing the medicaments. For example, if one seed occupied a 1 mm, 10 mm long tube, the estimated radioactive source would be about 1 to 4 mm cubed whereas if the entire tube was filled with radioactive sources as in a liquid; the radioactivity would occupy 31 mm cubed in volume. The volume would be greater if multiple tubes are welded or otherwise gathered together (e.g., to form a ribbon) in a custom fit to a particular tumor-excision site or treatment site.

Generally, the vehicles are hollow wires having various cross sections adapted to receive fluidized medicaments. To accommodate the treatment of tiny lumens such as ducts, medicament delivery vehicle cross sections of between 1 mm and 10 mm are suitable.

Given the small diameter of the wires, medicament may be loaded therein via capillary action. Then, over time, medicament such as chemotherapeutic agents, antibiotic or other topically-operable drugs may exit either pores or both ends of the wire, via osmosis or surface tension created by contact between the ends and adjacent mucosa.

However, in the case of brachytherapy, after wire loading, the ends of the wire may be sealed so as to prevent direct exposure of radioisotope to body tissue. Further, the vehicle may be selected to confer partial radioactive shielding. For example, nitinol wire shaped memory polymers or other materials, may be used to prevent over exposure or the development of hot spots at treatment sites.

The wire vehicle may define be a continuous, unbroken cavity into which is deposited the chosen medicament. As such, the wire vehicle has a first end and a second end. One such vehicle is that depicted in FIGS. 1B, 1C, 3A, 3B, and 4, discussed below.

Alternatively, the wire vehicle may be discontinuous along its length such that it has a first end, a second end, a first intermediate end and a second intermediate opposing the first intermediate end. Such a device is depicted in FIG. 1A. A sleeve may overlay the first and second intermediate ends and in slidable communication therewith. This allows for the wire to be extended at its first and second ends while still conferring radioactive shielding to mucosa proximal to the sleeve, and perhaps in physical contact with the sleeve.

FIG. 1A depicts a basic component of the invented system, generally designated as numeral 10. FIG. 1 depicts a tubular shaped vehicle 12 partially encircled by a sleeve 20. A first end 14 and second end 16 of the vehicle protrudes from opposite ends of the sleeve. Intermediate ends 18 of the vehicle oppose each other and are overlaid by the sleeve 20. The sleeve may be in slidable communication with the vehicle. This sliding feature allows the spiral, originally overlaid by the sleeve, to be uncovered so as to expand in diameter. The sleeve provides additional shielding from over exposure to radiation contained in the already attenuating vehicles.

The construct depicted in FIG. 1A is shown partially deployed. However, when the construct is manipulated so that more of the vehicles are nested within the sleeve, the sleeve will serve as additional attenuating substrate to prevent over radiation from the vehicles 12 crowded within the sleeve. Alternatively, the sleeve 20 may be fixed to portions of the vehicle 12 to prevent sliding and confer permanent coverage/shielding to that region of the vehicle. This permanent shielding will prevent medicament overexposure of mucosa 22 situated proximal to the sleeve 20. When spiral vehicles are used, the sleeves 20 allow increasing spiral radial diameter in portions of the device without necessarily increasing or decreasing the length of the spiral or the construct.

The vehicle is filled with free flowing medicament, such as chemo-therapy fluids, fluid radio-isotopes, etc. As discussed supra, if the vehicle is filled with radio-isotopes, the vehicle should be hermetically sealed to prevent leakage. An advantage of liquid filled vehicles is that the spiral dimensions of the vehicle may be tighter so as to pass through smaller lumens.

FIG. 1A depicts the vehicle 12 as a tube with a circular cross section. However, the vehicle may also define an oval cross section, a square cross section, a triangular cross section, a rectangular cross section or some other polygonal shape.

The delivery mechanism may further comprise a plurality of vehicles positioned relative to each other to mimic the shape of its resting place (e.g., the tumor excise cavity) within the body. For example a plurality of tubes may be gathered together to form a flat substrate. This would be particularly effective if the cross section of the tubes were actually rectangular or square as opposed to circular, so as to allow dense packing of the tubes against each other to form a sheet.

Spiral Detail

FIG. 1B shows a spiral shaped vehicle 13 for encapsulating fluidized medicaments such as liquid or gaseous radio-isotopes or a liquid-gas mixture. A gap "g'" extending parallel to the longitudinal axis of the spiral and defined by adjacent hoops of the spiral provides a means for maintaining flowage of liquids through the lumen, such as a duct. Depending on the type of material forming the spirals, memory shape material may cause larger gaps to form in vivo when the vehicle is subjected to body temperatures. Spirals defining smaller gaps or spirals absent any gaps may be utilized when lumen impairment is less of a concern or problem. Spirals may have varying radial diameters at multiple locations along its length to accommodate varying target shapes.

The longitudinal gap "'g" will vary depending on many circumstances and situations. Generally, gap distances may vary from 0 mm to 10 mm.

FIG. 1C depicts a spiral shaped vehicle 13 encircling the periphery of a bone support rod 15 or other structure. The vehicle 13 may be fully or partially embedded into the surface of the rod. In such partial embedment, the vehicle is countersunk relative to the surface of the rod and reversibly adhered thereto so as to be removed, replenished, or replaced. For example, the ribbon or other device fits in a groove on the surgical rod. The rod may further be encircled by the sleeve 20 depicted in FIG. 1A.

The iteration depicted in FIG. 1C also provides a means to decrease external beam radiation. Usually when an orthopedic device e.g. rod is placed across a pathologic fracture in a long bone the entire bone and much soft tissue is included in the volume. The metal rod also partially shields the cancerous tissues. Also, the integral radiation dose is high. By wrapping or otherwise incorporating radioisotopes with the rod, less radiation is necessary to treat the same tissue. Furthermore, if clinically indicated, additional devices (e.g., external beam boost, etc.) could be added to ensure adequate treatment of the cancerous tissues.

FIG. 2 depicts a vertebral column as a potential treatment venue for a plurality of medicament delivery vehicles illustrated in FIG. 3A-B. Each vehicle 24 defines a triangular shaped cross section, arranged to form a circle. The center of the circle further comprises a balloon 26 or other means for biasing each of the vehicles to the periphery of the circle when the balloon is inflated or the means is actuated.

Commercially available balloons, such as those used for orthopaedic applications are suitable for this aspect of the invention. For example, Kyphon™ brand balloons (Medtronic Spinal and Biologics, Inc, Memphis, Tenn.) are inflatable bone tamps (IBT) that have maximum rated inflation pressures of e.g., 700 psi when used with its inflation syringe. Such features are preferred in kyphoplasty applications discussed supra. A myriad of balloon sizes and volumes are available (e.g., 10 mm/3 cc, 15 mm/4 cc and 20 mm/5 cc) and in access profiles of about 10 gauge. Other means may include a permeable saline bag that inflates due to osmosis. Preferably, these medicament vehicle actuation means are biocompatible.

In this treatment scenario, an access opening 30 to a collapsed vertebrae 28 is provided. The medicament delivery construct 23 is injected or otherwise placed within the vertebrae in its deflated or undeployed configuration FIG. 3A. The construct is shown as a plurality of vehicles, each vehicle sized in similar, straight lengths depending on the treatment site and cavity. For example, in kyphoplasty applications, the vehicles may each be about e.g., two cm in length. Spirals may also be used in combination with the straight lengths, or in replacing the straight lengths.

Once positioned inside of the vertebrae 28, the balloon 26 is actuated and the individual vehicles are biased in a radial direction (FIG. 3B) until they contact the interior surfaces of the hollowed-out vertebrae. In this iteration, the shaped devices fill the iatrogenically produced volume. As such, the radio-isotope filled vehicle defines a netting or framework of sorts lining the interior of the periphery. Fluid under pressure may be injected into the balloon to expand the vertebra and the space filled with cementum. In one scenario, the cementum resides within the void such that the medicament filled vehicle is positioned between the cementum filled void and the interior surfaces of the vertebrae.

Ribbon Detail

The wires may be combined to form structures such as ribbons. In such instances, the eventual flexible planar structures, for example may be about 5 mm wide and about 1 mm in height or thickness. This will render a medicament reservoir or volume of about 50 $mm^3$.

Specifically, wires with a circular or non-circular cross section may be arranged side by side to form a plane or ribbon. Alternatively, a single vehicle with a single, continuous, uninterrupted or un-partitioned cavity may be employed as depicted in FIG. 4B.

Longitudinally extending gaps between the individual ribbons may or may not exist in vivo. Alternatively the wires and or ribbons may be positioned next to each other such that no gaps exist when the construct is positioned in the body, but gaps later form due to the body heating up the memory shaped substrate. This formation of gaps is multi-fold in purpose, including expanding stent shape to the boundaries of any tumor excision cavity to confer maximum treatment of adjacent tissue.

A pattern of hollow ribbons can cover a tiny structure with a small impingement on the lumen. In certain situations such as such as cholangial pancreatic ducts any narrowing can lead to sludging, congestion, or partial obstruction. Coating of the interior wall may decrease this risk. Some stent devices can be placed via duodenal retrographic approach, ERCP retroduodenography, or extra hepatic percutaneous placement. A biocompatible adhesive may be placed on the exterior of the device to adhere to the adjacent tissue, thereby reducing risk of slippage with the adjacent tissue.

Figure 4B:
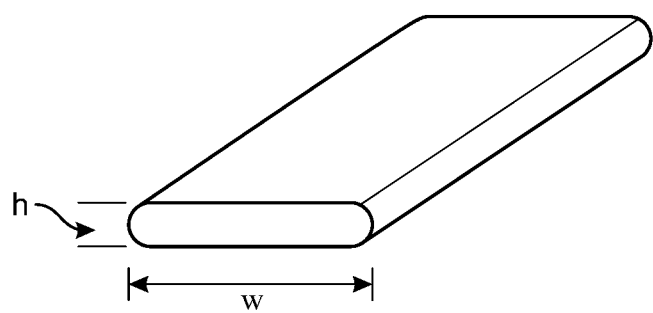
FIG. 4B is a perspective view of a single brachytherapy vehicle shaped as a ribbon, in accordance with features of the present invention.

FIG. 4A is a perspective view of a medicament delivery system 40 comprising a plurality of conduits 12 arranged in parallel. The final configuration of this delivery system is ribbon-like, so as to be reversibly flexible. To maintain the ribbon or flat configuration, a frame 42 or adhesive is applied to the top, bottom or peripheral surfaces "s" of the ribbon. Alternatively or in addition, the conduits may be fixed in place relative to each other by welding, adhesive wrap 44, such as film comprising polyvinyl chloride (PVC), polyethylene (PE), polyolefin (POF), and combinations thereof. The wrap may completely encircle the ribbon. An alternative is to have a hollow ribbon defining a single continuous unbroken void, e.g., an inner cross section with dimensions of 5 mm by 1 mm. It is envisioned that the entire device have a memory shape.

FIG. 4A depicts the conduits have a circular cross section but other geometric shapes are also suitable, as discussed supra. Further the conduits may each define a spiral.

Also, while FIG. 4A depicts straight conduits in parallel with each other, the entire ribbon may be contorted such that the conduits are not straight but perhaps define a curve, a spiral as mentioned above, or a sine wave configuration. Furthermore, tubes forming the longitudinal periphery of the ribbon may be peeled away from the frame 42 or adhesive if the surgeon requires a more narrow stent. These features allow the device to be conformed to whatever duct or excise site is being treated.

FIG. 4B shows a single void space ribbon iteration, the void space is defined by a single vehicle having cross section with a height at a fraction of its width. For example, the a cross section measurement of 0.5-1 mm high "h" by 3-6 mm in width "w" is suitable.

Ribbon-like vehicles confer advantages over prior art designs. For example, ribbons decrease tubular skin distortions inasmuch as the ribbons have a relatively thinner profile. Depending on the material used (e.g., nitinol) comprising the individual medicament vehicles, the final forms may have a memory shape. This will allow the surgeon to place the vehicle into the excision space with the anticipation that overtime, the vehicle may revert to its more compacted or expanded configuration as a consequence of its contact with mucosa defining the periphery of the excision space.

Figure 5B:
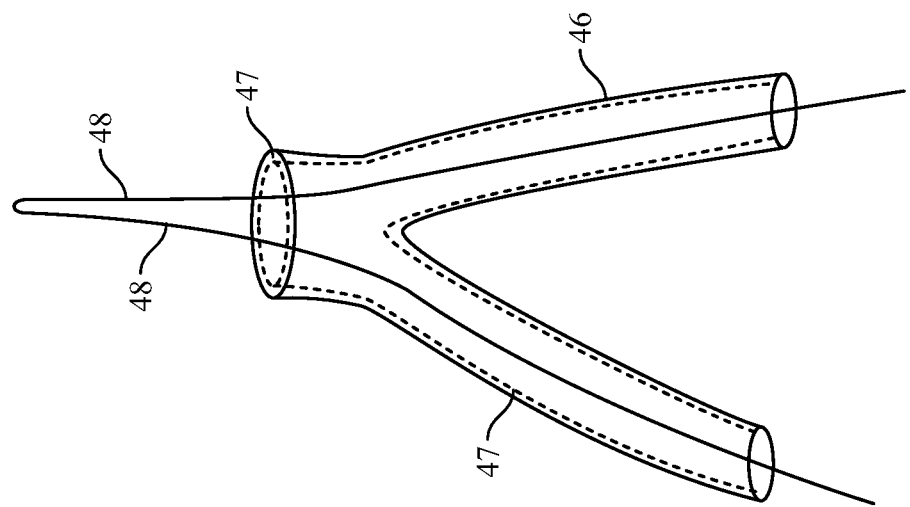
FIG. 5B shows a bifurcated medicament vehicle deployed over a guide wire, in accordance with features of the present invention.
Figure 5A:
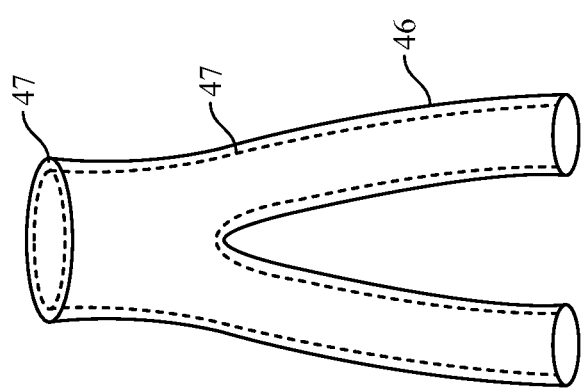
FIG. 5A shows an undeployed bifurcated medicament vehicle, in accordance with features of the present invention.

Bifurcated and trifurcated devices maybe used when the tracheal carina, bronchial bifurcations and other sites such as hepatic duct bifurcations (Klatskin's tumor) are treated. FIG. 5 is an example of a bifurcated vehicle 46. FIG. 5A shows a pre-deployed vehicle. FIG. 5B shows a bifurcated vehicle conforming to guidewires 48. The bifurcated or trifurcated device may feature a distal taper.

The bifurcation/trifurcation is meant to irradiate a tumor or vasculature (including arterio venous shunts) that crosses anatomical bifurcations to deliver a uniform radiation dose avoiding overlap/underlap situations. This may also decrease the likelihood of dislodgement by e.g. coughing retching etc. As such, it is a double walled device defining an annular space 47 adapted to receive medicament, for example fluidized radioisotope. As with other vehicles described herein, the open ends of the annular spaces may be sealed with biocompatible adhesive, wax, solder, heat or UV welding, crimping, or other means. Generally, when working with radioisotopes having long half-lives, these sealing means should withstand the physiologic and chemical environments of the body so as to assure the isotopes remain sequestered within the walls of the vehicle.

The device could be a solid tube or a spiral. In these situations, the device may be passed through an endoscope or possibly via guidewires or other means. The guidewires may be passed through each bronchus and the preformed device slid over the wire, possibly under the scrutiny of fluoroscopy. Once the device is in place, the guide wire may be removed.

Medicament and Loading Detail

Loading of the afore-described conduits is straight forward, and may include the use of capillary action, pressure injection, or simple immersion of the vehicles in the selected liquid medicament for a time to cause the medicament to migrate to all regions of the conduit. The then loaded delivery system is inserted into the treatment or tumor excise site. The benefit of the ribbon configuration depicted in FIG. 4 is that the ribbon may allow for a thinner stent wall, a smoother stent, larger internal volume, and therefore less interruption of the passage of bodily fluids.

The incorporation of liquid medicaments allows multiple vehicle shapes, even irregular asymmetrical ones. This allows the physician to fill in defects. Also, preloaded vehicles allows the surgeon to be shaped in surgery by the physician.

Another advantage of using fluid radio-isotopes is the dissemination of the radiation sources adjacent to or within a delivery conduit. This essentially decreases the dose gradient within the conduit. Furthermore, if the delivery conduit comprises nitinol metal, that metal will filter undesirable lower energy radiations, to further minimize over exposure of healthy tissue. Typical therapeutic dosage energies range from 20 kev to about 100 kev. Lower energies (e.g., 20 to 60 kev) allow the patient to be in public with relatively simple shielding. Higher energies (e.g., above 70 kev) require the patient to wear special shielding to protect others. Radiation is delivered over weeks or months to a year in the low dose rate treatment scenarios. This effect is biologically different when radiation is delivered over a very short period of time.

Also, fluid isotopes, such as liquid isotopes allows increased flexibility as to the selection of delivery canisters, including the use of spiral configurations smaller than possible when prior art solid radio-isotope seeds were used. Embodiments of the spiral may include loosely wound spirals or tightly wound spirals. Loosely wound spirals define gaps between the spiral loops. This allows for less impairment or blockage of the physiological lumen, so as to allow continued physiological function. Tightly wound spirals define very small or no gaps between their loops and may be used when lumen impairment is not an issue. These smaller configurations allow treatment of similarly smaller tubular luminal structures, and without gaps between coplanar ribbons, if so desired. As such, the ribbons may be positioned side by side to provide a continuous surface emanating therapeutic radiation.

Physiologic luminal structures envisioned for treatment with the invented system include those of the esophageal, colon, gastric, bronchial, biliary, pancreatic, and vascular structures.

The usually preloaded catheters as described above may be inserted into after-loading catheters of the types depicted in FIGS. 6A-D. Semi-circular after loading catheters 52 (FIG. 6A) and notched semi-circular after loading catheters 54 (FIG. 6B) are suitable, particularly in efforts to minimize or eliminate the creation of hot spots on mucosa and other healthy tissue. With the semi-circular after loading catheter, a wire 12 full of liquid medicament is slidably received by the catheter, thereby "loading" the catheter. The volume included by the shaped, after loaded catheters could then be expanded (by inflating a balloon centrally located within the after loaded catheter) to fill the desired space. A notch 60 may be provided to decrease any potential hotspot at that location of the after-loading catheter.

After-loading catheters with a square shaped cross section 56 (FIG. 6C) may be suitable, wherein a portion of the interior of the catheter is filled with radiation attenuation material 57. Similarly, an ovoid after-loading catheter (FIG. 6D) may contain a mass of attenuation material 57. The attenuation material may be adhered to one longitudinally extending interior surface of the after-loading catheter via adhesive, heat weld, chemical weld, or similar means. Alternatively, the attenuation material may be integrally molded with the after-loading catheter. Medicament filled wires 12 or ribbons slidably interact with these catheters, thereby nesting within the after-loaded catheters.

Figure 6A:
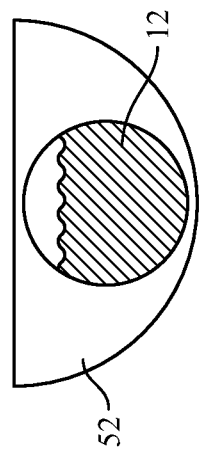
FIG. 6A depicts an after-loaded catheter defining a semi-circular cross section, in accordance with features of the present invention.
Figure 6B:
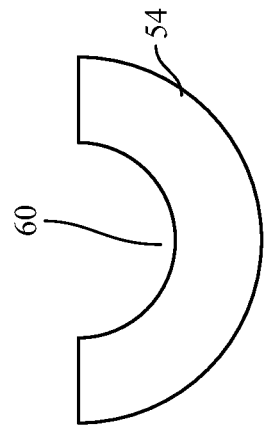
FIG. 6B depicts an after-loaded catheter defining a cut our or notch to form a U-shaped cross section, in accordance with features of the present invention.
Figure 6C:
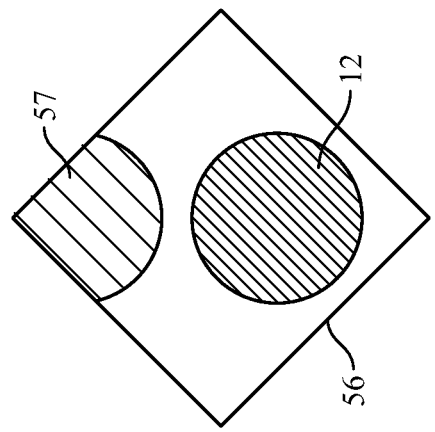
FIG. 6C depicts an after-loaded catheter defining a square cross section, in accordance with features of the present invention.
Figure 6D:
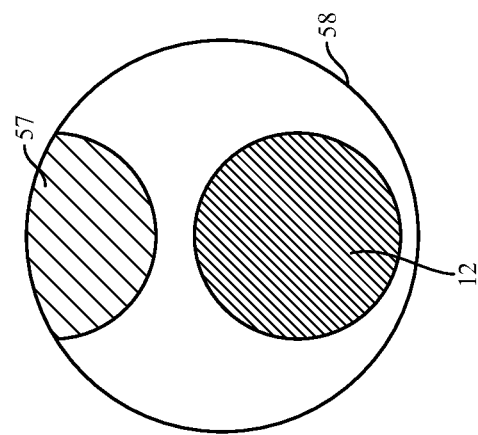
FIG. 6D depicts an after-loaded catheter defining an ovoid-shaped cross section, in accordance with features of the present invention.

It will be appreciated that the conduits need not be fully loaded with fluid medicament. Rather, the conduits 12 may be partially filled, as depicted in FIG. 6A, so that between 10 and 80 percent of the conduits are full of fluid medicaments. This may result in the establishment of a head space above the fluid. In the case of fluid radio-isotopes, partial filling will aid in attenuating dosage and therefore minimize the formation of hot spots proximal to the head space that would otherwise form on mucosa lining the treatment site.

In another iteration, plastic tubing can have a nitinol ribbon dictating the shape.

In the case of brachytherapy, a myriad of radio-isotopes are available as fluidized means for radioactivity. Suitable isotopes are those that are in fluid phase with Kev ranges of between approximately 20 Kev to about 600 Kev, and preferably between 20 Kev and 110 Kev. For example, radio-isotopes selected from the group consisting of Iridium 192, Iodine 125, Cesium 131, Samarium 153, Palladium 103, and combinations thereof are suitable. Other isotopes having similar key ranges may be used when they become available.

In operation, any of the aforementioned configurations are first loaded with medicament. Then, the configurations are form fitted to the treatment site and either surgically implanted in the site or injected there via a syringe or interventional radiology devices. (Interventional radiology uses image-guided technology such as X-rays, fluoroscopic CT scans, and MRI to perform minimally invasive procedures.)

The vehicles may be later harvested once dosage is delivered, or else left in the body for possible passage, eventual decomposition via physiologic means such as plasma pH levels, microphage action, or just left in situ.

The vehicles may be utilized singly or as a plurality. While the sizes of the vehicles will depend on their ultimate use, the inventor envisions vehicle lengths ranging from 5 mm to 100 mm, and vehicle cross section diameters ranging from 0.5 mm to 50 mm.

In summary, the invention provides a method for delivering and positioning medicaments into the body, the method comprising encapsulating free flowing radio-isotope into a vehicle and positioning the vehicle into the body. The vehicle may comprise radioactive shielding material. A salient feature of the method is that the medicament is a fluid, and particularly a liquid.

The vehicle sequestering the medicament is a semi rigid material selected from the group consisting of metals such as nitinol, platinum, stainless steel, tungsten, their various alloys, memory shaped substrates, coated polymers, and combinations thereof. The vehicle may comprise a plurality of tubes wherein the tubes are parallel with each other. The tubes have a first end and a second end and the tubes each have a cross section with a geometric shape selected from the group consisting of a circle, a square, a triangle, a rectangle, an oval, and combinations thereof. (Nitinol-comprising vehicles with these cross sections are commercially available, for example from Fort Wayne Metals, Fort Wayne, Ind.) Furthermore, the vehicles may be moved relative to each other after the vehicles are placed in the body. The step of positioning the vehicle in the body comprises interventional radiographic means or injecting the vehicle into the body with a syringe.

The invention also provides a system for delivering and positioning radio-isotopes into the body, the system comprising free flowing fluid radio-isotope encapsulated in an elongated substrate. The step of positioning the ribbon in the body comprises inserting the ribbon into the body via a vehicle selected from the group consisting of syringe, needles, trocars, endoscopic instruments, interventional radiology techniques, and combinations thereof. The substrate may be semi-radio-opaque. In embodiments of the system, the substrate is a plurality of conduits, each conduit defining a cross section shape selected from the group consisting of a circle, a square, a triangle, a rectangle, and combinations thereof. Each of the conduits may be movable in situ relative to each other.

The substrate may be shaped as a spiral (or a tube or other shapes) having a first end and a second end, a first intermediate end and a second intermediate end, whereby the first and second intermediate ends oppose each other. The first and second intermediate ends may be overlaid by a sleeve. The sleeve may slidably communicate with the spiral. The sleeve may be radio-opaque. The first and second intermediate ends may be overlaid by the sleeve.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A method for delivering and positioning radio-isotopes into a body, the method comprising:
   a. encapsulating a free flowing fluid-phase radio-isotope into a single cavity hollow ribbon that is unpartitioned to establish a continuous and homogeneous radiation dose distribution, wherein the ribbon comprises material to minimize radiation over-exposure of healthy tissue; and
   b. positioning the ribbon into a lumen of the body.

2. The method as recited in claim 1 wherein the ribbon comprises radioactive shielding material selected from the group consisting of nitinol, platinum, stainless steel, tungsten, coated polymers, memory shaped substrates, and combinations thereof.

3. The method as recited in claim 1 wherein the radio-isotope is a gas.

4. The method as recited in claim 1 wherein the radio-isotope is a liquid.

5. The method as recited in claim 1 wherein the radio-isotope is a mixture of liquid isotopes and gaseous isotopes.

6. The method as recited in claim 1 wherein the ribbon is a semi rigid material selected from the group consisting of nitinol, memory shaped polymer, alloy, and combinations thereof.

7. The method as recited in claim 1 wherein the ribbon comprises a plurality of tubes wherein the tubes are parallel with each other.

8. The method as recited in claim 7 wherein the tubes have a first end and a second end and each of said tubes has a cross section with a geometric shape selected from the group consisting of a circle, a square, a triangle, a rectangle, an oval, and combinations thereof.

9. The method as recited in claim 7 wherein the tubes are moved relative to each other after the ribbon is placed in the body.

10. The method as recited in claim 1 wherein the step of positioning the single cavity hollow ribbon in the body comprises inserting the ribbon into the body via a vehicle selected from the group consisting of: a syringe, needles, trocars, endoscopic instruments, interventional radiology techniques, and combinations thereof.

11. The method as recited in claim 1 wherein the material is a semi rigid material selected from the group consisting of nitinol, platinum, stainless steel, tungsten, their various alloys, memory shaped substrates, coated polymers, and combinations thereof.

* * * * *